US011504350B2

(12) United States Patent
Levine et al.

(10) Patent No.: US 11,504,350 B2
(45) Date of Patent: Nov. 22, 2022

(54) CANNABINOID COMPOSITIONS AND METHODS OF USE THEREOF

(71) Applicant: IZUN PHARMACEUTICALS CORP., New York, NY (US)

(72) Inventors: William Z. Levine, Jerusalem (IL); Shimon Lecht, Petah Tikva (IL); Olga Gabay, Jerusalem (IL)

(73) Assignee: DAY THREE LABS MANUFACTURING INC., Denver, CO (US)

( * ) Notice: Subject to any disclaimer, the term of this patent is extended or adjusted under 35 U.S.C. 154(b) by 398 days.

(21) Appl. No.: 16/758,857

(22) PCT Filed: Oct. 24, 2018

(86) PCT No.: PCT/IL2018/051134
§ 371 (c)(1),
(2) Date: Apr. 24, 2020

(87) PCT Pub. No.: WO2019/082181
PCT Pub. Date: May 2, 2019

(65) Prior Publication Data
US 2020/0289460 A1    Sep. 17, 2020

Related U.S. Application Data

(60) Provisional application No. 62/576,685, filed on Oct. 25, 2017.

(51) Int. Cl.
*A61K 31/352* (2006.01)
*A61P 25/20* (2006.01)
*A61K 31/05* (2006.01)
*A61K 36/185* (2006.01)
*A61K 9/00* (2006.01)

(52) U.S. Cl.
CPC ............ *A61K 31/352* (2013.01); *A61K 31/05* (2013.01); *A61K 36/185* (2013.01); *A61P 25/20* (2018.01); *A61K 9/007* (2013.01); *A61K 9/0043* (2013.01); *A61K 9/0053* (2013.01)

(58) Field of Classification Search
CPC .... A61K 31/352; A61K 31/05; C07D 311/80; C07C 15/46

USPC ................... 514/455, 734; 549/427; 568/807
See application file for complete search history.

(56) References Cited

FOREIGN PATENT DOCUMENTS

WO     2018173049     9/2018

OTHER PUBLICATIONS

Albert J. Siemens et al.: "Effect of cannabis on pentobarbital-induced sleeping time and pentobarbital metabolism in the rat" Biochermcal Pharmacology. vol. 23, No. 3, pp. 477-488, Feb. 1, 1974.
Bo Angela Wan et al.: "Efficacy of different varieties of medical cannabis in relieving symptoms" Journal of Pain Management, vol. 10, No. 4, pp. 375-383; Jan. 31, 2017.
Steep Hill: "Cannabinol (CBN): A Sleeping Synergy" online blog, retrieved from: https://www.steephill.com/blogs/34/Cannabinol-(CBD):-A-Sleeping-Synergy; Aug. 2, 2017.
Witschi, H. P., and Saint-Francois, B. "Enhanced Activity of Benzpyrene Hydroxylase in Rat Liver and Lung After Acute Cannabis Administration"(1972). Toxicol. Appl. Pharmacol. 23, 165-168.
Dhow, Edward, et al. "Efficacy of different varieties of medical cannabis in relieving symptoms in post-traumatic stress disorder (PTSD) patients." Journal of Pain Management 10.4 (2017): 415-422.
Chaves Rodrigo "Tikun Olam Taste Test—Freedom Leaf: Freedom Leaf". Oct. 1, 2018 (Oct. 1, 2018) https://www.freedomleaf.com/tikun-olam-marijuana-taste-test/.
Paton, William DM, and Roger Guy Pertwee. "Effect of cannabis and certain of its constituents on pentobarbitone sleeping time and phenazone metabolism." British journal of pharmacology 44.2 (1972): 250.
Leah Drost, BSc(C), et all. Efficacy of different varieties of medical cannabis in relieving symptoms in post-traumatic stress disorder (PTSD) patients //J Pain Manage, Feb. 2017;10(4):1-7.

*Primary Examiner* — Jeffrey H Murray
(74) *Attorney, Agent, or Firm* — JMB Davis Ben-David

(57) ABSTRACT

Embodiments relate to a method for treatment of a sleep disorder and to compositions comprising tetrahydrocannabinol (THC), cannabidiol (CBD), and cannabinol (CBN), wherein the ratio of THC:CBD:CBN by weight is A:B:C where A is between 0.0001 and 1, B is 1, and C is between 0.05 and 1. Optionally A is between 0.001 and 0.02, B is 1 and C is between 0.2 and 0.7.

20 Claims, 8 Drawing Sheets

CANNABINOID COMPOSITIONS AND METHODS OF USE THEREOF

CROSS REFERENCE TO RELATED APPLICATIONS

This is the US National Stage of International Patent Application No. PCT/IL2018/051134, which in turn claims the benefit to under 35 U.S.C. § 119(e) of U.S. Provisional Patent Application 62/576,685 filed Oct. 25, 2017; the contents of which are incorporated by reference herein in their entirety.

BACKGROUND

Cannabis is a genus of plants comprising the species *Cannabis sativa*, *Cannabis indica*, and *Cannabis ruderalis*. *Cannabis* plants have been cultivated for a variety of uses including making fibers (hemp), medicinal use and recreational drug use. *Cannabis* is also commonly known as marijuana.

One of the most common ways that *cannabis* is used for medicinal use in many countries (also known as medical marijuana) is through combustion of *cannabis* plant materials thus releasing active molecules, which may be through smoking. Alternatively, the *cannabis* plant materials can be vaporized, which may be achieved using dedicated equipment that heats *cannabis* plant materials to defined temperatures where boiling (vaporization) of active molecules occurs. Smoking *cannabis* is typically performed by using a pipe, by using a water-pipe (also known as a bong) which filters the smoke through water before inhalation or by rolling in paper to form marijuana cigarettes, also known colloquially as "joints." The part of the plant typically used for smoking is the whole flower and budding leaf.

Cannabinoids are compounds active on cannabinoid receptors in humans. Cannabinoids of plant origin, also known as phyto-cannabinoids, are abundant in plants of the *Cannabis* genus. Two known cannabinoids which are present in relatively high concentrations in *Cannabis sativa* are tetrahydrocannabinol-acid (THCA) or its decarboxylated product tetrahydrocannabinol (THC) and cannabidiolic acid (CBDA) or its decarboxylated product cannabidiol (CBD). Psychoactive and other medical effects of many of the cannabinoids have been studied. For example, THC was found to have psychoactive (calming) effects, analgesic effects, antioxidant effects and to increase appetite. CBD was found to have neuroprotective effects and to have ameliorative effects in patients with schizophrenia and Parkinson's disease.

In addition to cannabinoids, terpenoids and flavonoids are present in *cannabis* species. Exemplary terpenoids present in *cannabis* plant matter include Beta-myrcene and alpha-pinene.

SUMMARY

An aspect of an embodiment of the disclosure relates to a method of treating a cannabinoid-responsive condition, the method comprising administering to a subject in need thereof a therapeutically effective amount of a combination of tetrahydrocannabinol (THC), cannabidiol (CBD), and cannabinol (CBN). In an embodiment of the disclosure, the ratio of administered THC:CBD:CBN by weight is A:B:C where A is between 0.0001 and 1, B is about 1, and C is between 0.05 and 3. Optionally, A is between 0.0003 and 1, between 0.001 and 0.08, about 0.00033, about 0.00125, about 0.0125, about 0.075, or about 0.75. Optionally, C is between 0.2 and 2.5, about 0.07, about 0.25, about 0.5 about 2, and about 2.5.

In a particular embodiment, A is about 0.00033, B is about 1, and C is about 0.07. In another particular embodiment, A is about 0.00125, B is about 1, and C is about 0.5. In another particular embodiment, A is about 0.00125, B is about 1, and C is about 0.25. In another particular embodiment, A is about 0.00125, B is about 1, and C is about 2. In another particular embodiment, A is about 0.0125, B is about 1, and C is about 0.25. In another particular embodiment, A is about 0.075, B is about 1, and C is about 0.25. In another particular embodiment, A is about 0.75, B is about 1, and C is about 2.5.

In an embodiment of the disclosure, the method further comprises administering one or more terpenes or flavonoids.

In an embodiment of the disclosure, the method further comprises administering at least one further cannabinoid that is not a THC, a CBD, or a CBN. Optionally, the at least one further cannabinoid is whole-plant *cannabis* extract.

In an embodiment, the subject is a human subject.

In an embodiment, the dosage of THC administered is between 0.05 milligrams (mg) and 3 mg of the compound per kilogram (kg) weight of the subject (mg/kg). Optionally, the dosage of the THC is a human equivalent dose (HED) thereof. In an embodiment, the dosages of one or more of THC, CBD, or CBN administered, respectively, in accordance with an embodiment of the disclosure are individually the same as or less than dosages administered for therapeutic purposes as known in the art.

In an embodiment of the disclosure, the method is a method for improving sleep. Optionally, improving sleep comprises one or more than one of: increasing sleep duration, shortening sleep onset, decreasing number of transient awakenings during a sleep session, normalizing sleep-awake cycles, improving sleep architecture, and improving parasomnia conditions. Optionally, improving sleep comprises treating a sleep disorder, optionally insomnia.

In an embodiment of the disclosure, the method comprises administrating to the subject a composition comprising tetrahydrocannabinol (THC), cannabidiol (CBD), and cannabinol (CBN), wherein the ratio of THC:CBD:CBN by weight is A:B:C, with the values of A, B and C being as described above with respect to the method according to embodiment of the disclosure.

Optionally, a composition comprises one or more of pharmaceutically acceptable excipients.

In an embodiment of the disclosure, the THC, the CBD and the CBN are packaged for administration separately or sequentially. Optionally, two or more of the THC, the CBD and the CBN are packaged for simultaneous administration.

In an embodiment of the disclosure, one or more of the THC, the CBD and the CBN is an isolated cannabinoid isolated from a plant matter source, a synthetic cannabinoid manufactured using chemical means, or present comprised in plant matter. Optionally, the plant matter is prepared from botanical raw materials by one or more of the following processes: pulverization, decoction, expression, extraction (including aqueous extraction, ethanolic extraction, super critical $CO_2$ extraction, butane extraction or other extraction processes).

In an embodiment of the disclosure, a composition is packaged, prepared and/or formulated in a dosage form appropriate for delivery via the pulmonary, nasal, per os, or mucosal routes of administration. The dosage forms can be but not limited to liquid, elixir, syrup, powder, semi-solid, solid/liquid capsule, gel, a tablet, soft-gel capsule, disintegrating tablet, patch. Optionally, the composition is packaged, prepared and/or formulated in a dosage form for parenteral administration, oral administration, sublingual administration, buccal administration, or inhalation. Optionally, the composition further comprises one or more carriers, solvent/s or co-solvents, functional and/or inactive excipients. Such dosage forms as noted above may be prepared in accordance with standard principles of pharmaceutical formulation, known to those skilled in the art.

Inhalation, via pulmonary administration, can be performed using a composition prepared for vaporization, nebulization, or a composition introduced into a metered dose inhaler.

Oral administration may be via a tablet, liquid filled capsule, a soft-gel capsule, or a solution, emulsion, suspension or syrup.

Compositions may be prepared for administration to the oral cavity. For example, an oral disintegrating tablet or film, or a buccal patch or oral spray may be prepared with the compositions.

Compositions may be prepared for administration via nasal route. For example, a nasal spray or nasal drops may be prepared with the compositions.

Other aspects of the disclosure relate to providing a composition in accordance with an embodiment of the disclosure. Optionally composition is for use as a medicament. Optionally, the compositions is for improving sleep, optionally treating a sleep disorder.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

Figure 1:
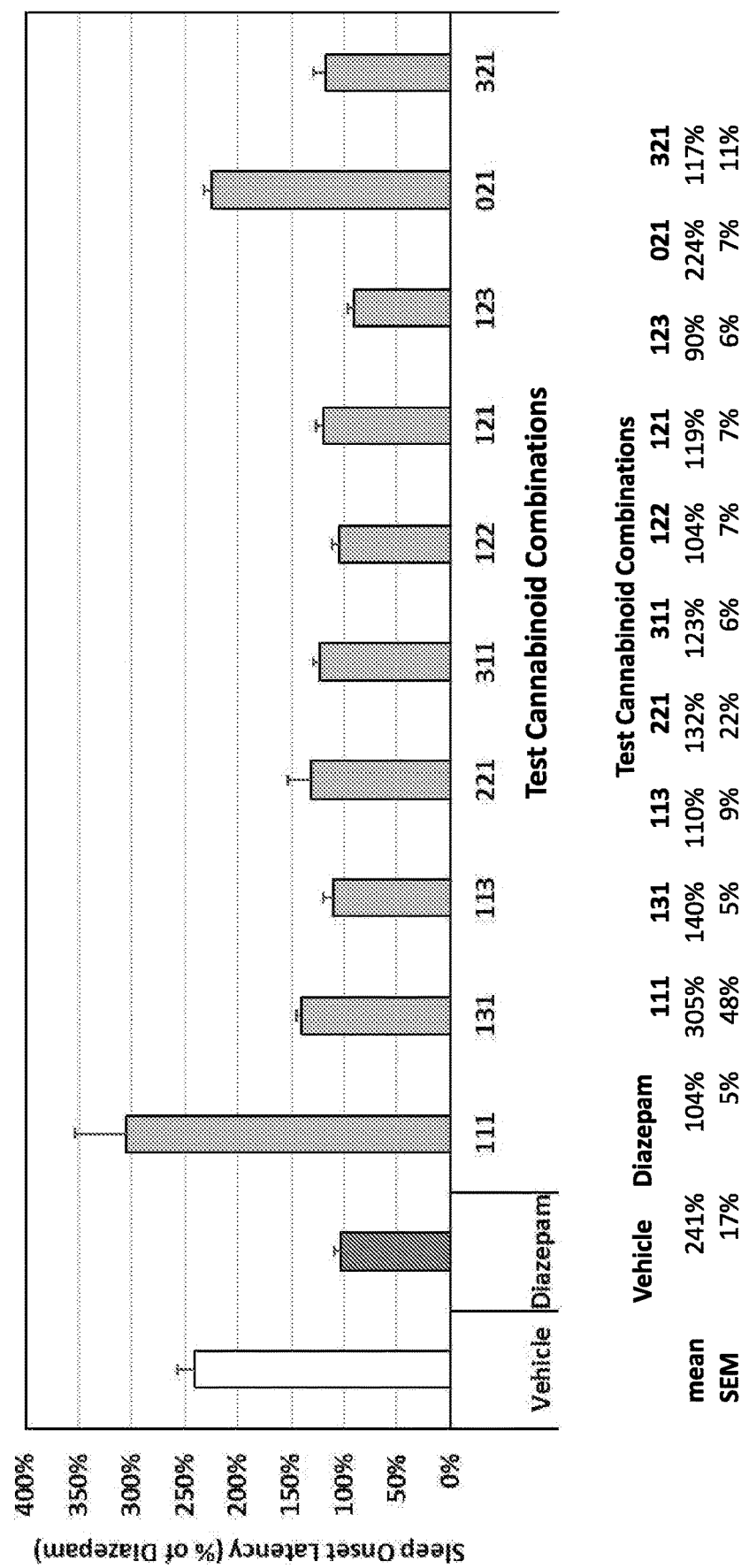
FIG. 1 shows a bar graph and data table showing results of total sleep duration in response to various cannabinoid compositions in accordance with embodiments of the disclosure.

Embodiments of the disclosure relate to a method for treatment of a sleep disorder, the method comprising administering to a subject in need thereof a therapeutically effective amount of a composition comprising a tetrahydrocannabinol (THC), a cannabidiol (CBD), and a cannabinol (CBN), wherein the ratio of THC:CBD:CBN by weight is A:B:C where A is between 0.0001 and 1, B is 1, and C is between 0.05 and 1. Optionally, A is between 0.001 and 0.02, B is 1 and C is between 0.2 and 0.7. Optionally, A is between 0.00125 and 0.0125, B is 1 an C is between 0.25 and 0.5. Optionally, A is 0.0025. Optionally, A is 0.00125. Optionally, C is 0.25. Optionally, C is 0.5. Optionally, C is 0.375. Optionally, the sleep disorder is selected from the group consisting of: decreased sleep duration, prolonged sleep onset, increased number of transient awakenings during a sleep session, aberrant sleep-awake cycles, aberrant sleep architecture, parasomnia, and insomnia. Optionally, the composition is free of terpenes. Optionally, the composition comprises a whole plant extract. Optionally, the composition is administered through the pulmonary, nasal, oral, or oral cavity route. Optionally, the composition is administered once daily. Optionally, the composition is administered within 1 hour before sleep. Optionally, the amount of CBD administered per day is between 0.375 and 3.75 mg per kg of bodyweight of the subject. Optionally, the amount of CBN administered per day is between 0.09375 and 1.875 mg per kg of bodyweight of the subject. Optionally, the amount of THC administered per day is between 0.4 and 50 micrograms per kg of bodyweight of the subject. Optionally, the composition comprises less than 5% of other cannabinoids relative to the combined weight of THC, CBD and CBN in the composition. Optionally, the composition comprises no cannabinoids other than THC, CBD and CBN.

Further embodiments relate to a composition comprising a tetrahydrocannabinol (THC), a cannabidiol (CBD), and a cannabinol (CBN), wherein the ratio of THC:CBD:CBN by weight is A:B:C where A is between 0.0001 and 1, B is 1, and C is between 0.05 and 1. Optionally, wherein A is between 0.001 and 0.02, B is 1 and C is between 0.2 and 0.7. Optionally, A is between 0.00125 and 0.0125, B is 1 an C is between 0.25 and 0.5. Optionally, A is 0.0025. Optionally, A is 0.00125. Optionally, C is 0.25. Optionally, C is 0.5. Optionally, C is 0.375. Optionally, the composition is for the treatment of a sleep disorder. Optionally, the composition comprises less than 5% of other cannabinoids relative to the combined weight of THC, CBD and CBN in the composition. Optionally, the source of a cannabinoid in the composition is whole plant extract. Optionally, the composition is prepared for administration via the pulmonary, nasal, oral, or oral cavity route. Optionally, the composition further comprises a carrier or an inactive ingredient.

Unless otherwise noted, technical terms are used according to conventional usage.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Definitions

Cannabinoid: a compound active on the cannabinoid receptor in a human. Preferably, a phytocannabinoid.

*Cannabis*: a plant from the family Cannabaceae, optionally *Cannabis sativa*, indica and *ruderalis*. Preferably a plant comprising a cannabinoid.

CBD: cannabidiol. A cannabinoid having the structure:

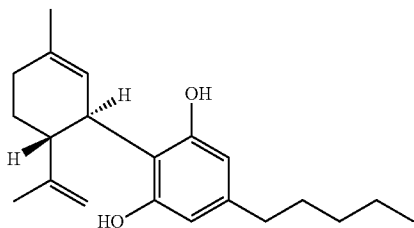 [SMILES: C=C(C)[C@@H]1CCC(C)=C[C@H]1c1c(O)cc(CCCCC)cc1O]

CBN: cannabinol. A cannabinoid having the structure:

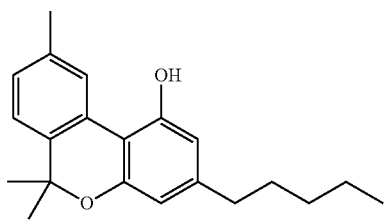 [SMILES: CCCCCc1cc(O)c2c(c1)OC(C)(C)c1ccc(C)cc1-2]

Sleep disorder: a condition in which sleeping patterns of a human are disrupted, impaired or otherwise pathologic. A sleep disorder may include: insomnia.

THC: tetrahydrocannabinol. A cannabinoid having the structure:

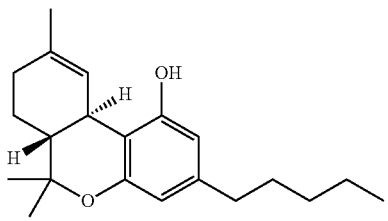 [SMILES: CCCCCc1cc(O)c2c(c1)OC(C)(C)[C@@H]1CCC(C)=C[C@@H]21]

Therapeutically effective amount: an amount, when administered to a human, shows a therapeutic effect, either upon acute or chronic administration.

The following examples are provided to illustrate certain particular features and/or embodiments. These examples should not be construed to limit the disclosure to the particular features or embodiments described.

Example 1: Effects of THC, CBD, CBN Compositions on Sleep

A study was conducted to measure the effects of compositions comprising cannabinoids THC, CBD, CBN on sleep latency and sleep duration using a well-established mouse model-based sleep test called the Loss Of Righting Reflex (LORR) test. The study identified compositions that exhibited positive effect in the aforementioned model.

The LORR test was used to study the effect of cannabinoid compositions on pentobarbital-induced sleep, and was conducted as follows: 30 minutes prior to sedation/sleep induction with an intraperitoneal (IP) injection of Pentobarbital (30 or 40 mg/kg), mice (7-week-old male Balb/C mice) were weighed and treated with an IP injection of: vehicle (Ethanol:Cremophor:Saline, volume ratio 1:1:18) as negative control; diazepam (3 mg/kg) as positive control; or with one of a plurality of test cannabinoid compositions in accordance with embodiments of the disclosure (described below). Observation of the mouse began immediately after administration of Pentobarbital. Once the mouse was asleep (as determined by the loss of righting reflex), it was transferred to a home cage and placed on its back, and observation was continued. Mice were considered awake when they could successfully upright themselves (all four feet in contact with the surface). Once a mouse righted itself, it was placed on its back once more and allowed to right a second time for confirmation. For the negative control group (vehicle treatment), mean sleep onset was 8-12 min and mean sleep duration was 25-45 min. For the positive control group (diazepam treatment), mean sleep onset was 3-5 min and mean sleep duration was 60-90 min. The 3 mg/kg dose of diazepam used in the mice is equivalent to approximately 10-12 mg dose in human subjects.

Test cannabinoid compositions were prepared using cannabinoids purified from whole *cannabis* plant extract, having >95% purity. The compositions were prepared in the aforementioned vehicle.

The test cannabinoid compositions contained two or more of THC at a dosage between 0.05 mg/kg (mg cannabinoid/kg weight of subject) and 3 mg/kg, CBD at a dosage of between 4 mg/kg and 150 mg/kg, and CBN at a dosage of between 10 mg/kg and 80 mg/kg. The following compositions were tested:

TABLE 1

| Composition # | Dosage in mg/kg | | |
|---|---|---|---|
| | THC | CBD | CBN |
| 111 | 0.05 | 4 | 10 |
| 131 | 0.05 | 150 | 10 |
| 113 | 0.05 | 4 | 80 |
| 221 | 0.5 | 40 | 10 |
| 311 | 3 | 4 | 10 |
| 122 | 0.05 | 40 | 20 |
| 121 | 0.05 | 40 | 10 |
| 123 | 0.05 | 40 | 80 |
| 021 | 0 | 40 | 10 |
| 321 | 3 | 40 | 10 |

The cannabinoid ratios of the tested compositions can be expressed as follows, with the relative concentration of THC arbitrarily set at 1 or 0, for ease of comparison of the relative amounts of the cannabinoids between the different compositions:

TABLE 2

| Composition # | Relative dosage ratio | | |
|---|---|---|---|
| | THC | CBD | CBN |
| 111 | 1 | 80 | 200 |
| 131 | 1 | 3000 | 200 |
| 113 | 1 | 80 | 1600 |
| 221 | 1 | 80 | 20 |
| 311 | 1 | 1 | 3 |
| 122 | 1 | 800 | 400 |
| 121 | 1 | 800 | 200 |
| 123 | 1 | 800 | 1600 |
| 021 | 0 | 4 | 1 |
| 321 | 1 | 13 | 3 |

Alternatively, the cannabinoid ratios of the tested compositions can be expressed as follows, with the relative concentration of CBD arbitrarily set at 1:

TABLE 3

| Composition # | Relative dosage ratio | | |
|---|---|---|---|
| | THC | CBD | CBN |
| 111 | 0.0125 | 1 | 2.5 |
| 131 | 0.00033 | 1 | 0.07 |
| 113 | 0.0125 | 1 | 20 |
| 221 | 0.0125 | 1 | 0.25 |
| 311 | 0.75 | 1 | 2.5 |
| 122 | 0.00125 | 1 | 0.5 |
| 121 | 0.00125 | 1 | 0.25 |
| 123 | 0.00125 | 1 | 2 |
| 021 | 0 | 1 | 0.25 |
| 321 | 0.075 | 1 | 0.25 |

The study included 12 mouse subjects treated with vehicle, 12 subjects treated with diazepam, and 6 subjects treated for each test cannabinoid composition.

FIG. 1 shows a bar graph and data table of the mean sleep onset latency for each tested composition, as a percentage of the mean sleep onset latency from the time of pentobarbital administration of subjects treated with diazepam. diazepam treated animals, as expected, fell asleep substantially faster following pentobarbital administration compare to those treated with vehicle (250% of latency with diazepam treatment). Animals treated with test cannabinoid compositions 111 and 021 exhibited sleep onset latencies similar to vehicle treatment (305% and 225% of diazepam treatment, respectively). Animals treated with the other compositions of 131, 113, 221, 311, 122, 121, 123, and 321 exhibited sleep onset latencies similar to diazepam treatment (between 140% and 90% of diazepam treatment).

Figure 2:
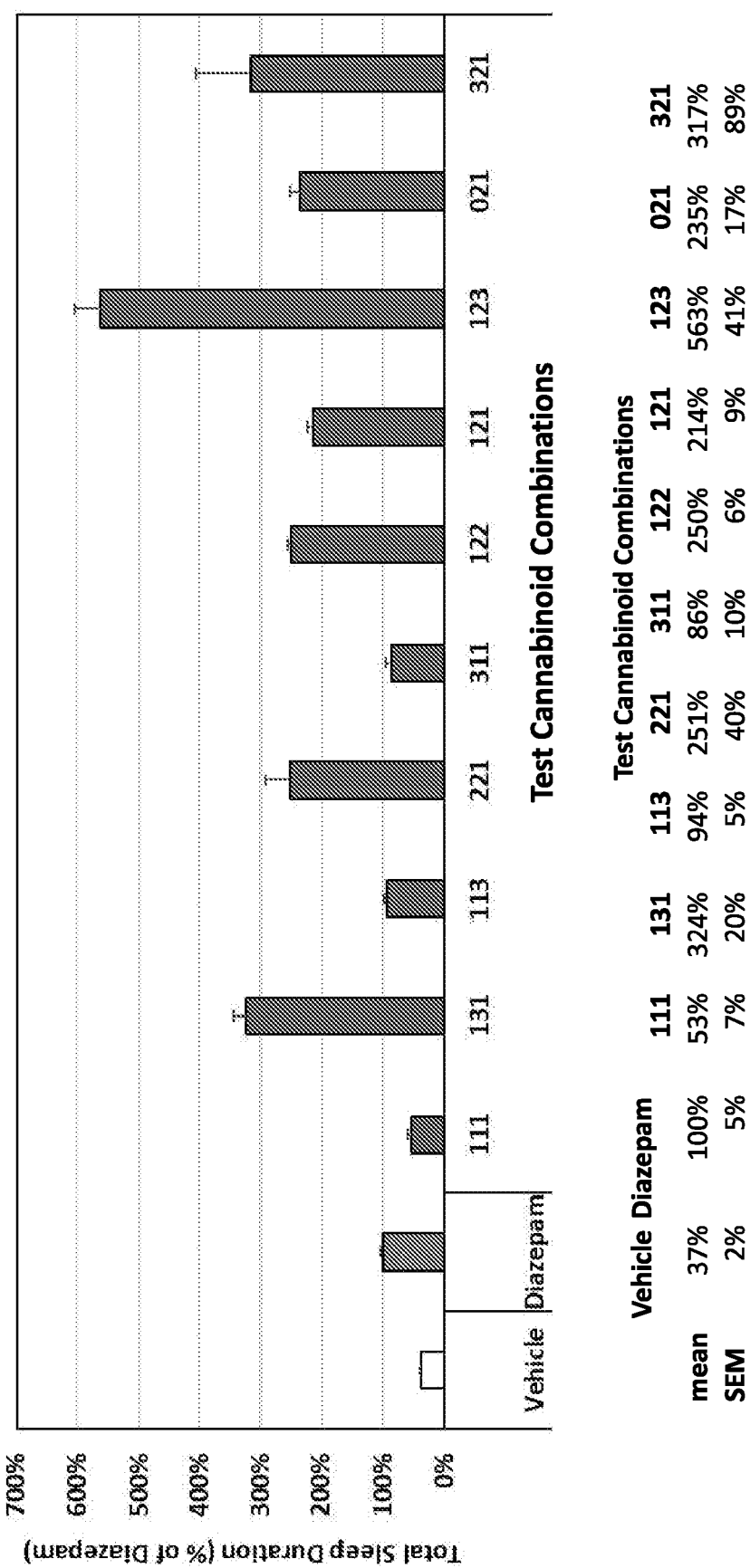
FIG. 2 shows a bar graph and data table of the mean total sleep duration in response to treatment with various cannabinoid compositions in accordance with embodiments of the disclosure.

FIG. 2 shows a bar graph and data table of the mean total sleep duration for each tested formulation, as a percentage of the mean total sleep duration of subjects treated with diazepam.

Diazepam treated animals, as expected, slept for a longer duration following pentobarbital administration compare to those treated with vehicle (37% sleep duration compared to diazepam treatment). Many of the test cannabinoid compositions were even more effective than diazepam in prolonging pentobarbital-induced sleep—compositions 131, 221, 122, 121, 123, 021 and 321 each exhibited a mean total sleep duration that was substantially longer than diazepam-treated controls (between 214% and 563% of diazepam treatment).

Figure 3:
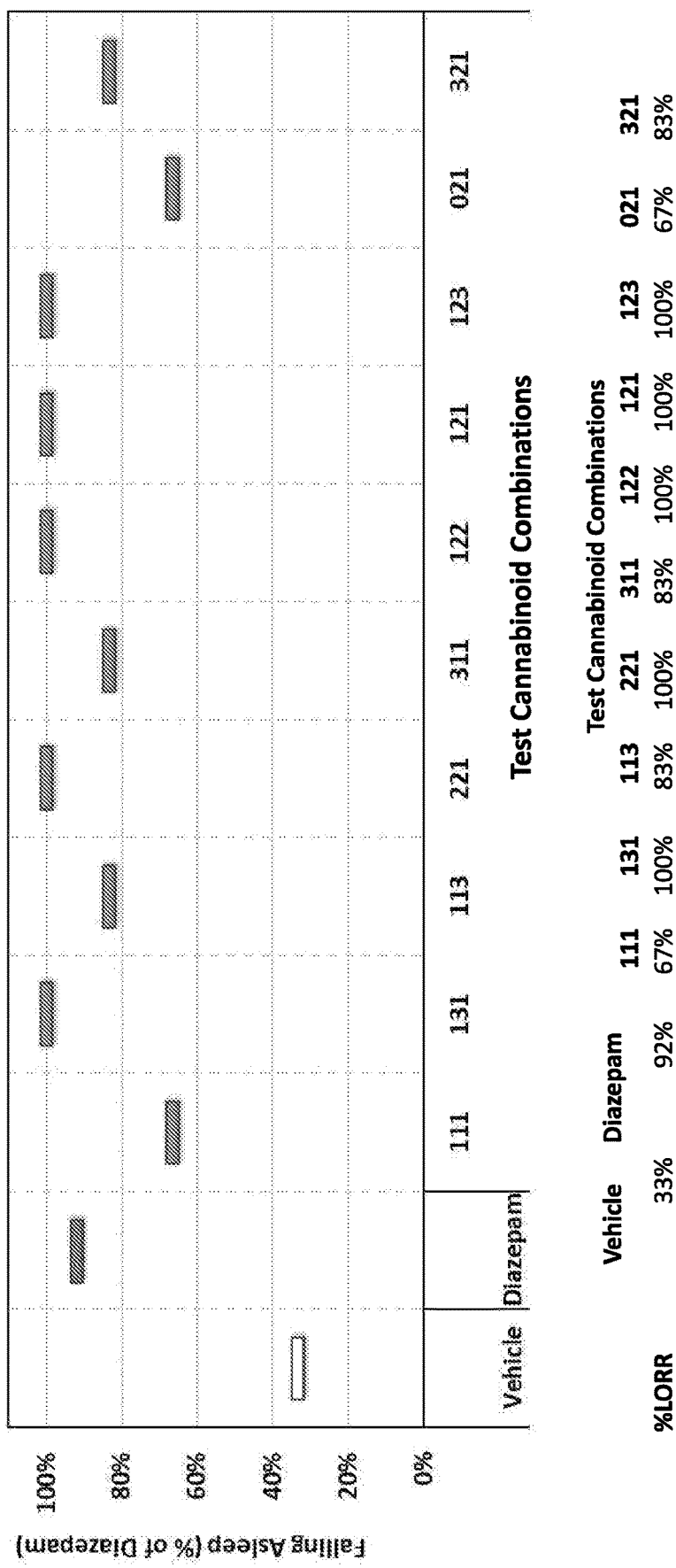
FIG. 3 shows a floating bar graph and data table showing the percentage of mice in each test group that fell asleep in response to treatment with various cannabinoid compositions in accordance with embodiments of the disclosure.

The pentobarbital dosing regimen induced sleep in only a portion of the vehicle-treated negative control mice. FIG. 3 shows a floating bar graph and data table of the percentage of mice in each treatment that fell asleep after pentobarbital administration. As shown in FIG. 3, 33% of vehicle treated mice fell asleep after pentobarbital treatment. Diazepam treatment enhanced the sleep-inducing effect of pentobarbital, such that 92% of diazepam-treated mice fell asleep after pentobarbital administration. Many of the test cannabinoid compositions were even more effective than diazepam in enhancing the sleep-inducing property of pentobarbital—compositions 131, 221, 122, 121 and 123 each had a 100% of mice in the treatment group fall asleep.

Figure 4:
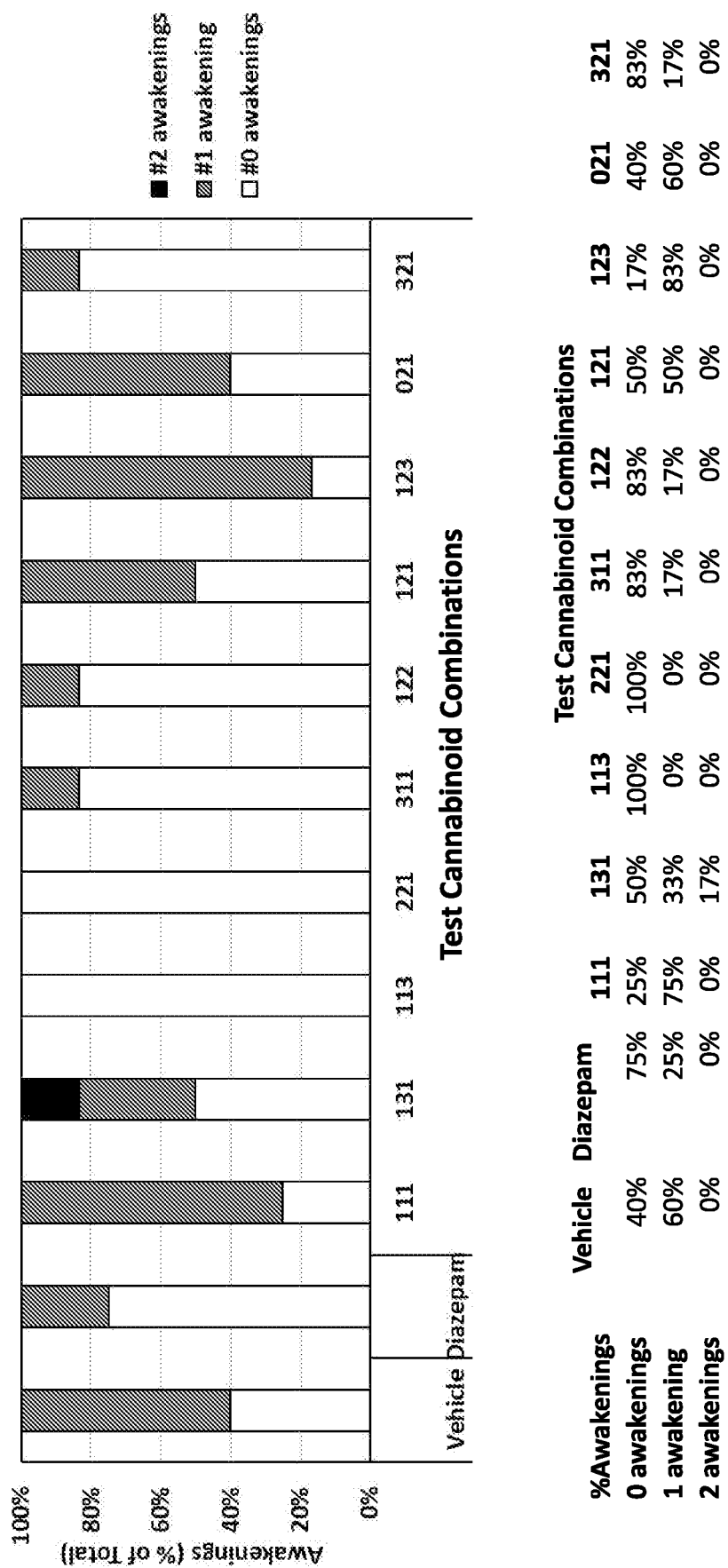
FIG. 4 shows a bar graph and data table showing the incidence of awakenings during a sleep session in response to various cannabinoid compositions in accordance with embodiments of the disclosure.

During the full course of pentobarbital-induced sleep, some of the subjects briefly woke up then fell back asleep, before fully waking up. FIG. 4 shows a bar graph and a data table showing the percentages of subjects in each test group that had 0, 1 or 2 brief, temporary ("transient") awakenings before fully awaking from the pentobarbital-induced sleep. When a mouse righted itself after pentobarbital treatment, the mouse was manually returned to a supine position to encourage the mouse to go back to sleep. If the mouse fell back asleep within three tries of being placed in the supine position, the mouse was evaluated as having not woken up. If the mouse did not return to sleep within the above three attempts, then the animal was allowed on its feet for 5-10 minutes, after which the mouse was returned to a supine position a maximum of three more times. If the mouse returned to sleep, then the brief waking episode was scored as a transient awakening. If the mouse still failed to go back to sleep, then the mouse was scored as being fully awake as of the time it righted itself.

Diazepam-treated animals, as expected, exhibited fewer transient awakenings compared to vehicle-treated negative controls. diazepam-treated subjects had lower incidence of transient awakenings during the respective sleep sessions. 60% of vehicle-treated subjects exhibited one transient awakening and 40% stayed asleep during the pentobarbital-induced sleep session. By contrast, out of the diazepam-treated subjects, 25% of the subjects woke up once and 75% stayed asleep during the sleep session. Many of the test cannabinoid compositions were as effective or more effective than diazepam in reducing the number of transient awakenings during the sleep session—groups treated with compositions 113, 311, 122, 221 and 321 had a higher incidence of sleep sessions with no transient awakenings (between 83% and 100%) compared to diazepam-treated controls.

Out of the test cannabinoid compositions tested using the LORR method, composition 122 had an especially favorable combination of sleep-enhancing properties. Subjects treated with a composition 122 had a mean total sleep duration 2.5-fold longer compared to diazepam controls while having fewer transient awakenings during the sleep session (83% of the group had no transient awakenings during the session compared 75% with diazepam treatment), and similar sleep onset latency compared to diazepam treatment.

Other examples of compositions with notably favorable combinations of sleep-enhancing properties include composition 131, composition 121, and composition 123.

Subjects treated with composition 123 had a mean total sleep duration 5.6-fold longer compared to diazepam controls and slightly shorter sleep onset latency compared to diazepam treatment. Composition 123 treatment resulted in having substantially more transient awakenings during the sleep session (17% of the group had no transient awakenings during the session compared 75% with diazepam treatment). Without being bound by theory, the increase in the incidence of transient awakenings indicates changes in the sleep architecture associate with this composition, in that while other compositions may induce deeper sleep stages the composition 123 induces relatively shallow sleep with sharp transition between sleep stages that observationally result with apparent awakening of the subject. Alternatively, and without being bound by theory, the increase in the incidence of transient awakenings in mice treated with composition 123 is reflective of the substantial increase in the duration of the sleep session, in which transient awakenings as measured per unit time (as opposed to during the entire sleep session). Mice treated with composition 123 exhibited, on average, a 3.3-fold increase in incidence of a transient awakening during their respective sleep sessions compared to diazepam-treated subjects (83% incidence of a transient awakening in composition 123 mice compared to 25% in diazepam-treated mice). However, this increase in mean incidence of transient awakening is offset by the 5.6-fold increased total sleep duration for composition 123-treated mice. As such, the mean incidence of transient awakening per unit time of sleep session duration is lower in composition 123-treated mice.

Subjects treated with composition 121 had a mean total sleep duration 2.1-fold longer compared to diazepam controls while having only slightly more awakenings during the sleep session (50% of the group had no awakenings during the session compared 75% with diazepam treatment), and slightly longer sleep onset latency of 1.2-fold longer compared to diazepam treatment.

Subjects treated with composition 131 had a mean total sleep duration 3.2-fold longer compared to diazepam-treated controls while having only slightly more awakenings during the sleep session (50% of the group had no awakenings during the session compared 75% with diazepam treatment), and only slightly longer sleep onset latency of 1.4-fold longer compared to diazepam treatment.

Without being bound by theory, differences between composition 021 and composition 121 with regard to sleep onset latency and percent of mice that fell asleep (FIGS. 1 and 3) seem to indicate that the presence of THC in small amounts relative to CBD and CBN increases the sleep-enhancing effect of the compositions relative to composition with CBD and CBN alone. Increase of amount of THC relative to CBD and CBN, as in composition 321 decrease total sleep duration in comparison to composition 121.

Example 2: Further Effects of THC, CBD, CBN Compositions on Sleep

The LORR model was performed as in Example 1, using compositions described in table 4. The test cannabinoid compositions contained two or more of THC at a dosage between 0.05 mg/kg and 0.1 mg/kg, CBD at a dosage of between 20 mg/kg and 40 mg/kg, and CBN at a dosage of between 1 mg/kg and 15 mg/kg. The following compositions were tested:

TABLE 4

| | Dosage in mg/kg | | |
|---|---|---|---|
| Composition # | THC | CBD | CBN |
| 2 2 0.5 | 0.5 | 40 | 1 |
| 1 1.5 0.5 | 0.05 | 20 | 1 |
| 1.5 1.5 1 | 0.1 | 20 | 10 |
| 1 1.5 1 | 0.05 | 20 | 10 |
| 1.5 2 1.5 | 0.1 | 40 | 15 |
| 1.5 2 1 | 0.1 | 40 | 10 |
| 1 2 1.5 | 0.05 | 40 | 15 |
| 2 2 1 | 0.5 | 40 | 10 |
| 1.5 2 1.5 | 0.1 | 40 | 15 |

The cannabinoid ratios of the tested compositions are expressed with relative concentration of CBD set at 1.

TABLE 5

| | Relative dosage ratio | | |
|---|---|---|---|
| Composition # | THC | CBD | CBN |
| 2 2 0.5 | 0.0125 | 1 | 0.025 |
| 1 1.5 0.5 | 0.025 | 1 | 0.05 |
| 1.5 1.5 1 | 0.005 | 1 | 0.5 |
| 1 1.5 1 | 0.0025 | 1 | 0.5 |
| 1.5 2 1.5 | 0.0025 | 1 | 0.375 |
| 1.5 2 1 | 0.0025 | 1 | 0.25 |
| 1 2 1.5 | 0.00125 | 1 | 0.375 |
| 2 2 1 | 0.0125 | 1 | 0.25 |
| 1.5 2 1.5 | 0.0025 | 1 | 0.375 |

The cannabinoid ratios of the tested compositions are expressed with relative concentration of THC set at 1 are shown in table 6.

TABLE 6

| | Relative dosage ratio | | |
|---|---|---|---|
| Composition # | THC | CBD | CBN |
| 2 2 0.5 | 1 | 80 | 2 |
| 1 1.5 0.5 | 1 | 400 | 20 |
| 1.5 1.5 1 | 1 | 200 | 100 |
| 1 1.5 1 | 1 | 400 | 200 |
| 1.5 2 1.5 | 1 | 400 | 150 |
| 1.5 2 1 | 1 | 400 | 100 |
| 1 2 1.5 | 1 | 800 | 300 |
| 2 2 1 | 1 | 80 | 20 |
| 1.5 2 1.5 | 1 | 400 | 150 |

The study included 12 mouse subjects treated with vehicle, 14 subjects treated with diazepam, 6 subjects treated for each test cannabinoid composition and 4 subjects in each terpenes-only group.

Figure 5:
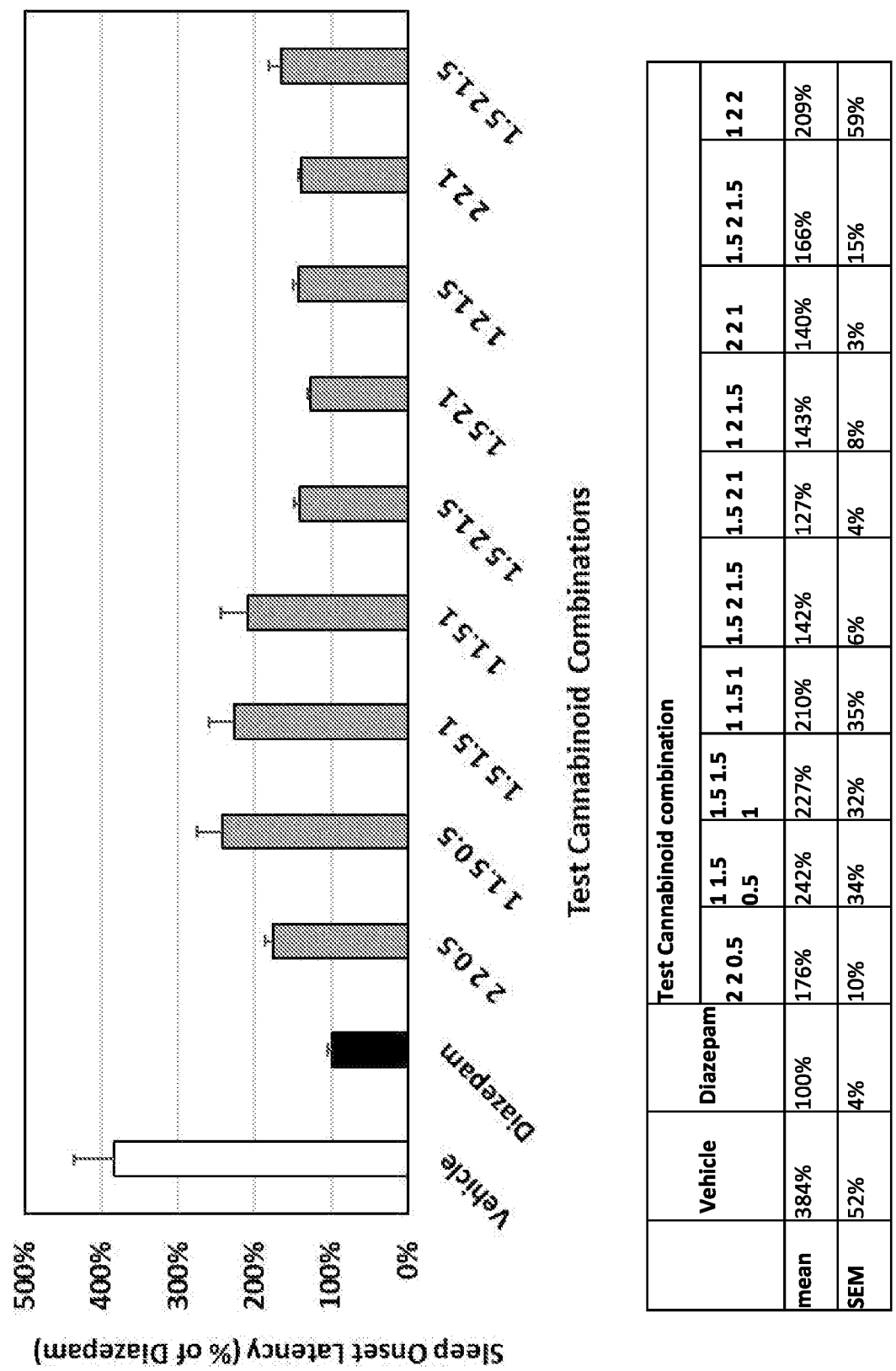
FIG. 5 shows a bar graph and data table showing results of total sleep duration in response to various cannabinoid compositions in accordance with embodiments of the disclosure.

FIG. 5 shows a bar graph and data table of the mean sleep onset latency for each tested composition, as a percentage of the mean sleep onset latency from the time of pentobarbital administration of subjects treated with diazepam. The vehicle-treated animals showed sleep latency of 384% relative to the diazepam-treated animals. All of the compositions comprising THC, CBD and CBN showed improved sleep onset latency in comparison to vehicle. Animals treated with test compositions 1.5 2 1.5, 1.5 2 1, 1 2 1.5 and 2 2 1, showed the best results, having mean sleep onset latency of less than 150% relative to diazepam.

Figure 6:
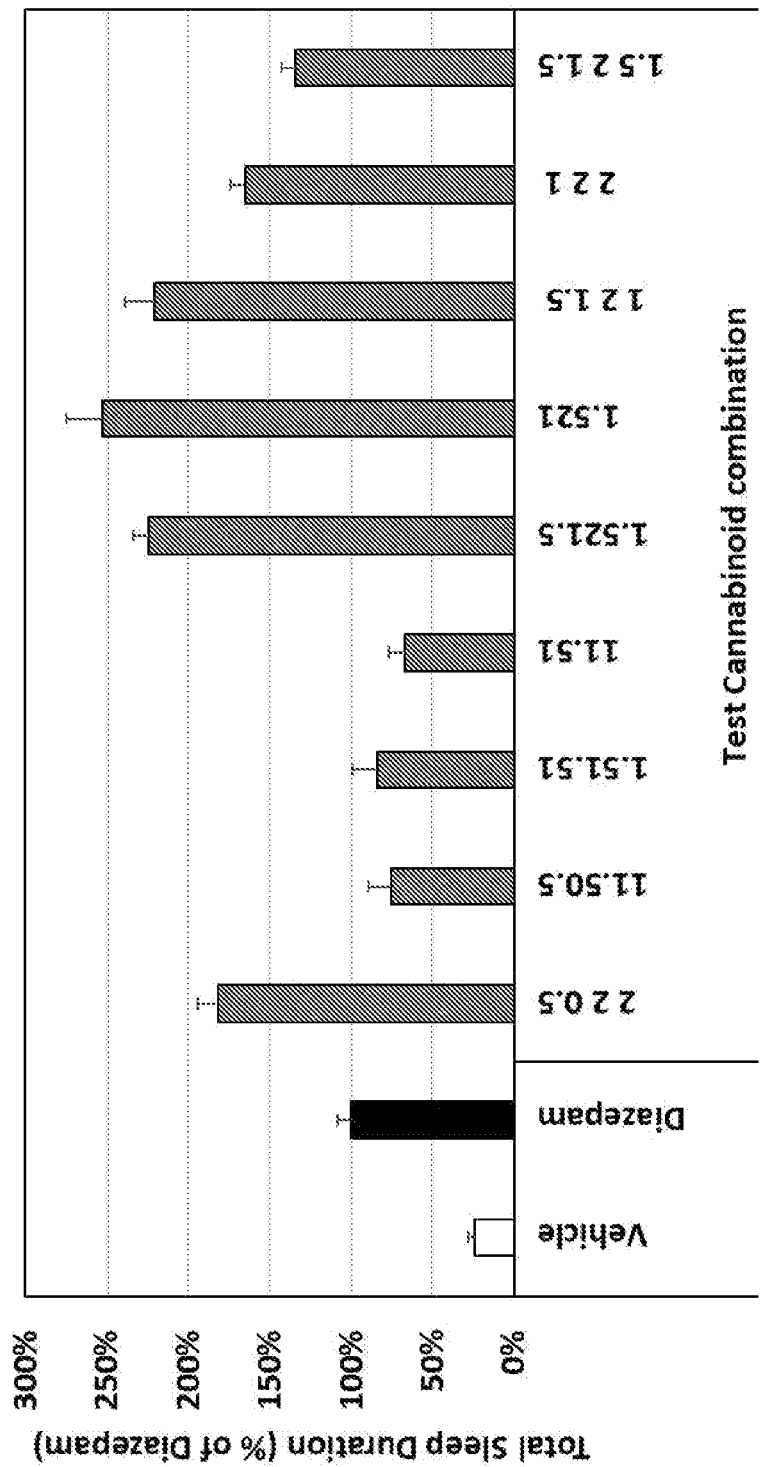
FIG. 6 shows a bar graph and data table of the mean total sleep duration in response to treatment with various cannabinoid compositions in accordance with embodiments of the disclosure.

FIG. 6 shows a bar graph and data table of the mean total sleep duration for each tested composition, as a percentage of the mean total sleep duration of subjects treated with diazepam. Diazepam treated animals, as expected, slept for a longer duration following pentobarbital administration compare to those treated with vehicle only (24% sleep duration compared to diazepam treatment). Many of the test cannabinoid compositions were even more effective than diazepam in prolonging pentobarbital-induced sleep—compositions 2 2 0.5, 1.5 2 1.5, 1.5 2 1, 1 2 1.5, 2 2 1, and 1.5 2 1.5 each exhibited a mean total sleep duration that was longer than diazepam-treated positive controls (between 134% and 252% of diazepam treatment).

Figure 7:
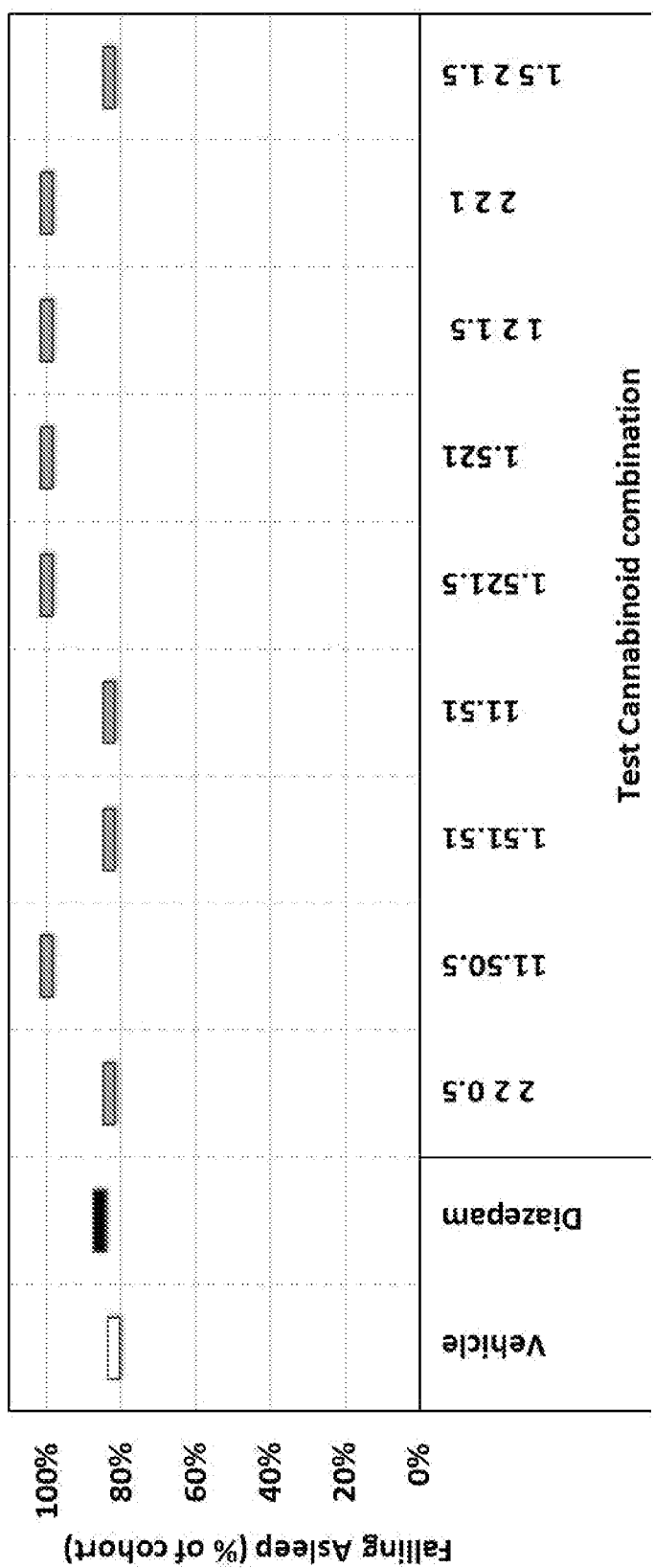
FIG. 7 shows a floating bar graph and data table showing the percentage of mice in each test group that fell asleep in response to treatment with various cannabinoid compositions in accordance with embodiments of the disclosure.

FIG. 7 shows a floating bar graph and data table of the percentage of mice in each treatment that fell asleep after pentobarbital administration (i.e., response rate to the treatment). As shown in FIG. 7, 82% of the test animals fell asleep in the vehicle group after pentobarbital treatment. Diazepam treatment enhanced the sleep-inducing effect of pentobarbital, such that 86% of diazepam-treated mice fell asleep after pentobarbital administration. Many of the test cannabinoid compositions were even more effective than diazepam in enhancing the sleep-inducing property of pentobarbital. Compositions 1 1.5 0.5, 1.5 2 1.5, 1.5 2 1, 1 2 1.5, and 2 2 1, each had 100% of mice in the treatment group fell asleep.

Example 3: Effects of Terpene-Containing Compositions on Sleep

A mixture of terpenes resembling the profile occurring in *Cannabis* strain "Grand Daddy Purple" was obtained. The profile of the terpenes was as listed in table 7.

TABLE 7

| Terpene | Percent | Milligrams per gram |
| --- | --- | --- |
| β- Caryophyllene | 9 | 90 |
| D-Limonene | 7.6 | 76 |
| α- Humulene | 3.5 | 35 |
| Linalool | 5.1 | 51 |
| β-Myrcene | 24 | 240 |
| α-Pinene | 50 | 500 |
| Total Measured: | 99 | 992 |

Composition 1 2 2 as in Example 1 was prepared, and was also prepared with the modification of addition of 0.1% v/v terpenes.

In addition, compositions with only terpenes at 0.001%, 0.01%, 0.1% and 1% v/v were prepared in the same aforementioned vehicle as cannabinoid-containing combinations (Ethanol:Cremophore:Saline).

Figure 8:
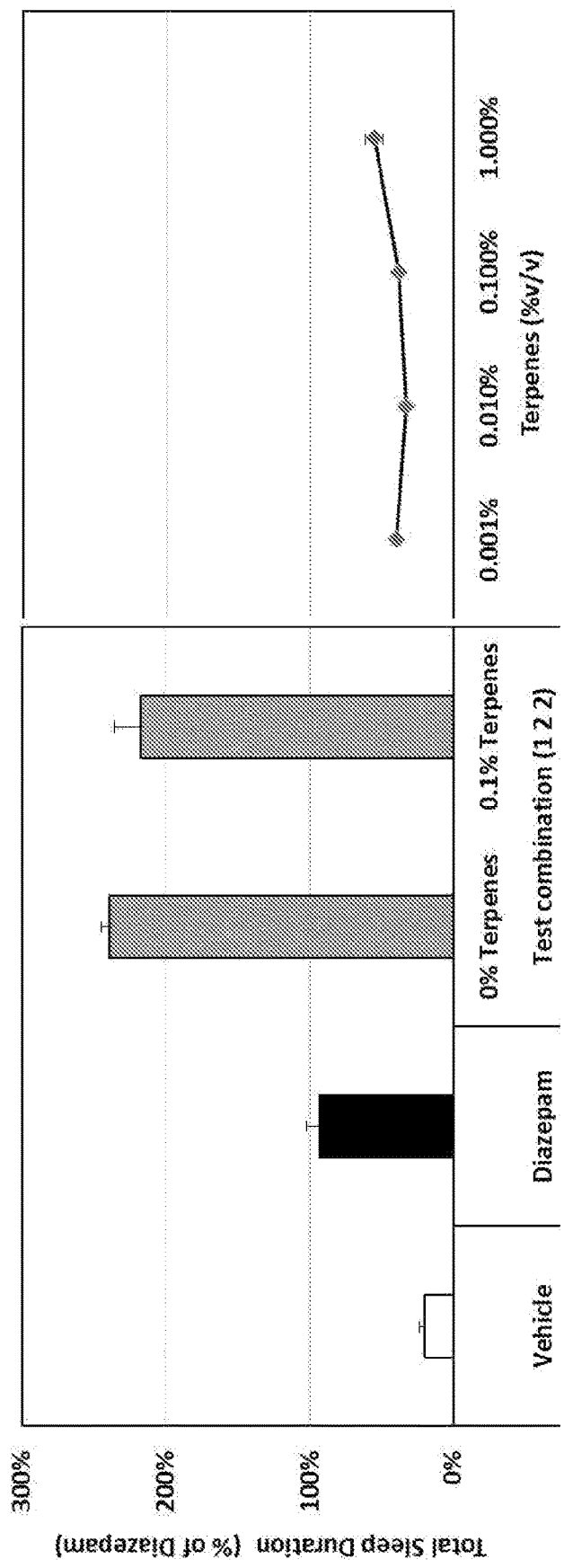
FIG. 8 shows a bar graph and data table of the mean total sleep duration in response to treatment with various cannabinoid compositions with or without terpenes, in accordance with embodiments of the disclosure.

FIG. 8 shows a bar graph, line graph and a data table of the mean total sleep duration for each tested composition, as a percentage of the mean total sleep duration of subjects treated with diazepam. The 1 2 2 composition showed improvement in total sleep duration relative to diazepam. When 0.1% v/v terpenes were added to the 1 2 2 composition, there was a slight decrease in total sleep duration. Terpenes alone, without CBD, THC and CBN, did not improve total sleep duration relative to diazepam.

Example 4: Naturally Occurring Compositions Comprising THC and CBD

Compositions comprising THC, CBD and CBN as described above do not occur in naturally occurring *cannabis* plant or in *cannabis* smoke or vapor. Tables 8-10 depict three common, representative *cannabis* strains, bedrocan, bedrobinol, and bediol. Presence of THC, CBD and CBN in plant matter extract obtained through ethanolic extraction (Table 8), vapor (Table 9) and smoke (Table 10) is shown. The source of the data in these tables is Fischedick, et al. Chem. Pharm. Bull. 58(2) 201-207 (2010).

TABLE 8

|  | Bedrocan | Bedrobinol | Bediol |
| --- | --- | --- | --- |
| THC (mg/g) | 220.8 | 110.1 | 67.6 |
| CBD (mg/g) | 0.79 | 0.39 | 85.6 |
| CBN (mg/g) | 0 | 0 | 0 |
| ratio of THC |  |  |  |
| THC | 1 | 1 | 1.0 |
| CBD | 0 | 0 | 1.3 |
| CBN | 0 | 0 | 0 |
| ratio of CBD |  |  |  |
| THC | 279 | 282 | 0.8 |
| CBD | 1 | 1 | 1.0 |
| CBN | 0 | 0 | 0 |

TABLE 9

|  | Bedrocan | Bedrobinol | Bediol |
| --- | --- | --- | --- |
| THC (mg/g) | 46.5 | 35.4 | 23.5 |
| CBD (mg/g) | 1.5 | 1.6 | 28 |
| CBN (mg/g) | 0.09 | 0.05 | 0.03 |
| ratio of THC |  |  |  |
| THC | 1 | 1 | 1.0 |
| CBD | 0 | 0 | 1.2 |
| CBN | 0 | 0 | 0 |
| ratio of CBD |  |  |  |
| THC | 31 | 22 | 0.8 |
| CBD | 1 | 1 | 1.0 |
| CBN | 0 | 0 | 0 |

TABLE 10

|  | Bedrocan | Bedrobinol | Bediol |
| --- | --- | --- | --- |
| THC | 36.2 | 26.7 | 17.6 |
| CBD | 0.54 | 0.1 | 21.1 |
| CBN | 6.9 | 3.5 | 2.9 |
| ratio of THC |  |  |  |
| THC | 1 | 1 | 1.0 |
| CBD | 0 | 0 | 1.2 |
| CBN | 0.2 | 0.1 | 0.2 |
| ratio of CBD |  |  |  |
| THC | 67 | 267 | 0.8 |
| CBD | 1 | 1 | 1.0 |
| CBN | 12.8 | 35.0 | 0.1 |

As seen in the tables, CBN does not exist in significant, detectable levels in *cannabis* plant matter or vapor. In *cannabis* smoke, some of the THC is converted into CBN. This indicates that compositions used in examples 1 and 2, having significant amounts of CBN relative to CBD, as described, do not occur in nature.

Example 5: Treatment of Humans Using THC, CBD and CBN Compositions

In treatment of humans, compositions may be administered via a variety of routes, with preference to the pulmonary, nasal, per os, and delivery via oral cavity. Compositions may be administered on a daily basis, or may be administered as per a patient's need. Compositions may be administered when sleep is desired. Optionally, compositions may be administered within 1 hour of desired bedtime.

Table 11 shows exemplary doses which may be used for treating humans according to methods described herein.

TABLE 11

| Composition | THC µg/kg | CBD mg/kg | CBN mg/kg |
|---|---|---|---|
| Range 1 | 0.4-100 | 0.1-5 | 0.05-2 |
| Range 2 | 0.4-10 | 0.375-3.75 | 0.09-1.4 |
| Composition A | 0.46875 | 0.375 | 0.1875 |
| Composition B | 0.46875 | 0.375 | 0.09375 |
| Composition C | 0.9375 | 0.375 | 0.09375 |
| Composition D | 0.9375 | 0.375 | 0.140625 |
| Composition E | 4.6875 | 3.75 | 1.875 |
| Composition F | 4.6875 | 3.75 | 0.9375 |
| Composition G | 9.375 | 3.75 | 0.9375 |
| Composition H | 9.375 | 3.75 | 1.40625 |

Indications which may be treated using compositions described herein include, but are not limited to sleep disorders. Such sleep disorders may be: Dyssomnia, parasomnia, or sleep disorder associated with mental, neurologic or other medical disorders.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for treatment of a sleep disorder, the method comprising administering to a subject in need thereof a therapeutically effective amount of a composition comprising a tetrahydrocannabinol (THC), a cannabidiol (CBD), and a cannabinol (CBN), wherein the ratio of THC:CBD:CBN by weight is A:B:C where A is between 0.0001 and 1, B is 1, and C is between 0.05 and 1.

2. The method according to claim 1 wherein A is between 0.001 and 0.02, B is 1 and C is between 0.2 and 0.7.

3. The method according to claim 2 wherein A is between 0.00125 and 0.0125, B is 1 an C is between 0.25 and 0.5.

4. The method according to claim 3 wherein A is 0.0025.

5. The method according to claim 3 wherein A is 0.00125.

6. The method according to claim 1 wherein C is 0.25.

7. The method according to claim 1 wherein C is 0.5.

8. The method according to claim 1 wherein C is 0.375.

9. The method according to claim 1 wherein the sleep disorder is selected from the group consisting of: decreased sleep duration, prolonged sleep onset, increased number of transient awakenings during a sleep session, aberrant sleep-awake cycles, aberrant sleep architecture, parasomnia, and insomnia.

10. The method according to claim 1 wherein the composition is free of terpenes.

11. The method according to claim 1 wherein the composition comprises a whole plant extract.

12. The method according to claim 1 wherein the composition is administered through the pulmonary, nasal, oral, or oral cavity route.

13. The method according to claim 1 wherein the composition is administered once daily.

14. The method according to claim 1 wherein the composition is administered within 1 hour before sleep.

15. The method according to claim 1 wherein the amount of CBD administered per day is between 0.375 and 3.75 mg per kg of bodyweight of the subject.

16. The method according to claim 1 wherein the amount of CBN administered per day is between 0.09375 and 1.875 mg per kg of bodyweight of the subject.

17. The method according to claim 1 wherein the amount of THC administered per day is between 0.4 and 50 micrograms per kg of bodyweight of the subject.

18. The method according to claim 1 wherein the composition comprises less than 5% of other cannabinoids relative to the combined weight of THC, CBD and CBN in the composition.

19. The method according to claim 18, wherein the composition comprises no cannabinoids other than THC, CBD and CBN.

20. A composition comprising a tetrahydrocannabinol (THC), a cannabidiol (CBD), and a cannabinol (CBN), wherein the ratio of THC:CBD:CBN by weight is A:B:C where A is between 0.0001 and 1, B is 1, and C is between 0.05 and 1.

* * * * *